US006812207B1

(12) United States Patent
Olson et al.

(10) Patent No.: US 6,812,207 B1
(45) Date of Patent: Nov. 2, 2004

(54) HEMOGLOBIN MUTANTS THAT REDUCE HEME LOSS

(75) Inventors: John S. Olson, Houston, TX (US); Timothy L. Whitaker, San Antonio, TX (US); Mark S. Hargrove, Houston, TX (US)

(73) Assignee: William Marsh Rice University, Houston, TX (US)

( * ) Notice: Subject to any disclaimer, the term of this patent is extended or adjusted under 35 U.S.C. 154(b) by 602 days.

(21) Appl. No.: 09/654,688

(22) Filed: Sep. 5, 2000

Related U.S. Application Data

(63) Continuation of application No. 09/051,872, filed as application No. PCT/US96/16934 on Oct. 23, 1996, now Pat. No. 6,114,505.
(60) Provisional application No. 60/006,020, filed on Oct. 23, 1995.

(51) Int. Cl.[7] .............................................. C07K 14/00
(52) U.S. Cl. .......................................... 514/6; 530/385
(58) Field of Search .............................. 530/385; 514/6

(56) References Cited

U.S. PATENT DOCUMENTS

| 4,873,192 A | 10/1989 | Kunkel | |
|---|---|---|---|
| 5,028,588 A | 7/1991 | Hoffman | |
| 6,022,849 A | * 2/2000 | Olson et al. | .................. 514/6 |

FOREIGN PATENT DOCUMENTS

| WO | WO 88/09179 | 12/1988 |
|---|---|---|
| WO | WO 90/13645 | 11/1990 |
| WO | WO 91/16349 | 10/1991 |
| WO | WO 91/19505 | 12/1991 |
| WO | WO 92/11283 | 7/1992 |
| WO | WO 92/22646 | 12/1992 |
| WO | WO 93/08831 | 5/1993 |
| WO | WO 95/07932 | 3/1995 |
| WO | WO 95/14038 | 5/1995 |
| WO | WO 96/27388 | 9/1996 |

OTHER PUBLICATIONS

Winterbourn et al. (1974), J. Clin. Invest. 54:678–689.
Ascoli et al. (1981), Meth. Enzymol. 76:72–87.
Fermi et al. (1984), J. Mol. Biol. 175:159–174.
Taylor et al. (1985), Nucl. Acids Res. 13:8749–8764.
Taylor et al. (1985), Nucl. Acids Res. 13:8765–8785.
Dente et al. (1985), pp. 101–107 in DNA Cloning.
Kunkel (1985), Proc. Natl. Acad. Sci. USA 82:488–492.
Nakamaye et al. (1986), Nucl. Acids Res. 14:9679–9698.
Bunn et al. (1986), Chapter 16, pp. 634–662 in Hemoglobin: Molecular, Genetic and Clinical Aspects.
Chatterjee et al. (1986), J. Biol. Chem. 261:9929–9937.
Kleinschmidt et al. (1987), J. Hoppe–Seyler's Z. Biol. Chem. 368:579–615.
Kunkel et al. (1987), Meth. Enzymol. 154:367–382.
Vincent (1989), Semin Hematol. 26:105–113.
Perutz (1989), Trends Biochem. Sci. 14:42–44.
Mathews et al. (1989), J. Biol. Chem. 264:16573–16583.
Hughson et al. (1990), Science 249:1544–1548.
Carver et al., (1990), J. Biol. Chem. 265:20007–20020.
Jones et al. (1990), BioTechniques 8:178–183.
Hoffman et al. (1990), Proc. Natl. Acad. Sci. USA 87:8521–8525.
Zhang et al. (1991), J. Biol. Chem. 266:24698–24701.
Jones et al. (1991), BioTechniques 10:62–66.
Mathews et al. (1991), J. Biol. Chem. 266:21631–21639.
Komiyama et al. (1991), Nature 352:349–351.
Yao et al. (1992), PCR Methods and Applications, 1:205–207.
Vandergriff (1992), Biotechnology and Genetic Engineering Reviews 10:403–453.
Fronticelli et al. (1993), Biochemistry 32:1235–1242.
Hargrove et al. (1994), Biochemistry 33:11767–11775.
Springer et al. (1994), Chem. Rev. 94:699–714.
Looker et al. (1994), Meth. Enzymol. 231:364–374.
Hargrove et al. (1994), J. Biol. Chem. 269–4207–4214.
Whitaker et al. (1995), Biochemistry 34:8221–8226.
Vandergriff (1995), pp. 105–131 in Blood Substitutes: Physiological Basis of Efficacy, Birkhauser, Boston.
Hargrove et al. (1996), Biochemistry 35:11293–11299.
Hargrove et al. (1996), Biochemistry 35:11300–11309.
Hargrove et al. (1996), Biochemistry 35:11310–11318.

* cited by examiner

*Primary Examiner*—Karen Cochrane Carlson
(74) *Attorney, Agent, or Firm*—Conley Rose, P.C.

(57) ABSTRACT

The present invention relates to methods of reducing heme loss in hemoglobins to produce stability and improve expression yield of hemoglobins, particularly recombinant hemoglobins. Such methods are accomplished by introducing mutations in the alpha or beta subunits of hemoglobins to increase heme affinity. The present invention further relates to novel mutations that reduce such heme loss.

7 Claims, No Drawings

HEMOGLOBIN MUTANTS THAT REDUCE HEME LOSS

REFERENCE TO RELATED APPLICATIONS

This application is a continuation of U.S. application Ser. No. 09/051,872, filed Apr. 22, 1998, now U.S. Pat. No. 6,114,505, which is a 371 of PCT/US96/16934, filed Oct. 23, 1996, which claims benefit to U.S. Provisional Application 60/006,020, filed Oct. 23, 1995.

FIELD OF THE INVENTION

This invention relates to mutant recombinant hemoglobins containing mutations which reduce the rate of loss of heme from the globin moiety. This invention further relates to improved yields of hemoglobin by expression of certain mutant subunits.

BACKGROUND OF THE INVENTION

The current blood banking system has inherent risks and serious limitations. Blood typing errors, transmission of bacterial agents, and viral infections such as HIV-1 and hepatitis A, B, and AB pose life threatening dangers to transfusion patients. In addition, availability of donors, requirement for specific blood types, short shelf life of red blood cells, and need for refrigeration all limit the accessibility of a transfusion to a patient. Development of a stable blood substitute could eliminate the risks of the current blood banking system and increase the availability of transfusions to patients in most environments.

In addition, an oxygen carrying blood substitute can increase and/or maintain plasma volume and decrease blood viscosity in the same manner as conventional plasma expanders, and can also support adequate transport of oxygen from the lungs to peripheral tissues. Moreover, an oxygen-transporting hemoglobin-based solution can be used in most situations where red blood cells or plasma expanders are currently utilized. An oxygen-transporting hemoglobin-based solution could also be used to temporarily augment oxygen delivery during or after pre-donation of autologous blood prior to the return of the autologous blood to the patent.

However, several obstacles must be overcome in the development of an optimal hemoglobin-based oxygen carrier, including: (1) inhibition of tetramer to dimer dissociation: (2) reduction of hemoglobin oxygen affinity; (3) inhibition of autooxidation; (4) inhibition of heme loss; and (5) increased stability of the apoglobin tertiary structures.

Thus far, most hemoglobin-based blood substitute designs have successfully focused on preventing tetramer dissociation and reducing oxygen affinity through chemical and genetic techniques (Winslow, R. M.(1992) *Hemoglobin-based Red Cell Substitutes*. The Johns Hopkins University Press, Baltimore 242 pp). Gawryl and coworkers (Gawryl, M., Clark, T., and Rausch, C., in *Red Cell Substitutes: The Proceedings of the Second International Symposium of Red Blood Cell Substitutes* (S. Sekiguchi, ed.) pp 28–40. Tokyo: Kindai Shupann, 1991) chemically cross-linked bovine hemoglobin using glutaraldehyde to prevent tetramer dissociation. Besides being very abundant, bovine hemoglobin was chosen because its oxygen affinity is regulated by chloride ions, and, as a result, has a relatively high $P_{50}$ value, which is the same inside or outside a red blood cell. Chatterjee et al. (Chatterjee. R., Welty, E. V., Walder, R. Y., Pruitt, S. L., Rogers. P. H., Arnone, A., and Walder, J. A. (1996) *J. Biol. Chem.* 261, 9929–9937) chemically crosslinked human hemoglobin using (3,5-dibromosalicyl) fumarate under conditions which also caused a two fold decrease in the oxygen affinity of the modified protein. A genetic approach is discussed by Hoffman et al., who used recombinant hemoglobin genes and an *E. coli.* expression system (Hoffman et al., WO 90/13645). They genetically linked the C-terminal residue of one alpha subunit to the N-terminus of the other alpha subunit using a flexible glycine residue, producing a single $alpha_1$-$alpha_2$ subunit (Looker, D., et al. *Methods in Enzymology* 231, 364–374, 1994). The tandem alpha globin gene was then combined with a copy of the beta globin gene and placed under the control of a single promoter to form a hemoglobin operon. To decrease the oxygen affinity, they also incorporated the Presbyterian mutation into the beta subunits. Presbyterian mutation refers to the beta(G10)Asp→Lys substitution which causes a reduction in oxygen affinity in both hemoglobin subunits. The final protein was designated rHb1.1 and has a $P_{50}$ value similar to that observed for intact red blood cells.

Inhibition of tetramer dissociation and alteration of oxygen affinity are only the first steps towards creating an optimal cell-free hemoglobin based blood substitute. The next step is to minimize the effects that may result from the instability of hemoglobin by increasing resistance to autooxidation, hemin loss, and apoglobin denaturation. Potentially toxic effects may result from the by products of autooxidation, free hemin, and insoluble apoglobins. These problems can include oxidative and peroxidative tissue damage and propagation of free radicals. (Vandegriff, K. D. (1995) in *Blood Substitutes: Physiological Basis of Efficacy* (Birkhauser, Boston) pp. 105–131). Moreover, the globin subunits that contain an oxidized iron or that have lost heme can no longer transport oxygen.

Hemoglobin is a tetrameric protein consisting of two alpha and two beta subunits and is the oxygen binding component in red blood cells. Each of the subunits is composed of a globin (protein portion) and a heme prosthetic group. Each of the globins fold into 8 alpha helices, labeled A through H, with the exception that alpha subunits lack five residues which correspond to the beta subunit D helix. The only nonhelical segments are the turns between helices. The positions of the amino acids are denoted by their position within a particular helix or their distance from the N-terminus. Hemoglobin subunits produced recombinantly by the methods described herein have an N-terminal methionine in place of the normally occurring N-terminal valine. The N terminus, regardless of identity is denoted as amino acid number 1.

In each globin, ligands bind to the $6^{th}$ coordination site of iron in the heme prosthetic group, protoporphyrin IX. The heme group is secured to the globin by a covalent bond between the $5^{th}$ coordination site of the heme iron and a proximal His(F8) residue. The ferrous or reduced state ($Fe^{+2}$) binds oxygen and carbon monoxide. The ferric form, known as methemoglobin, binds water, azide, cyanide, or hydroxide anions. When the iron in the protoporphyrin IX is reduced, the prosthetic group is denoted heme. On the other hand, when the iron is in the oxidized state in the protoporphyrin IX, the complex is called hemin.

Hemoglobin binds some ligands cooperatively. Cooperativity allows efficient $O_2$ uptake in the lungs where oxygen partial pressure is high and release in muscle capillaries where the partial pressure is much lower. Cooperative $O_2$ binding to hemoglobin is a result of allosteric interactions between the alpha and beta subunits.

The $alpha_1beta_1$ dimer is predominantly held together through strong hydrophobic interactions between the two subunits. Formation of the hemoglobin tetramer results from relatively weaker electrostatic interactions between two alpha$_1$beta$_1$ dimers, resulting in a tetramer with two new subunit interfaces called alpha$_1$beta$_2$ and alpha$_2$beta$_1$.

The hemoglobin tetramer can exist in either the T (low oxygen affinity) or the R (high oxygen affinity), quaternary conformation. In the absence of oxygen, hemoglobin is held in the T state by a lattice of electrostatic interactions at the alpha$_1$beta$_2$ and alpha$_2$beta$_1$ interfaces. Interconversion between the T and R states is accomplished by rotating the alpha$_1$beta$_1$ dimer 15° with respect to the alpha$_2$beta$_2$ dimer, or vice versa. The alpha$_1$beta$_1$ and alpha$_2$beta$_2$ interfaces are not affected by T to R interconversion, but formation of the R state requires disruption of a significant number of the electrostatic bonds in the T-state alpha$_1$beta$_2$ and alpha$_2$beta$_1$ interfaces.

Methemoglobin is formed by the oxidation of the heme iron from $Fe^{+2}$ to $Fe^{+3}$ (Winterbourn, C. C., and Carrel, R. W. *J. Clin. Invest*. 54, 678, 1977; Bunn, H. F., and Forget, B. G., *Hemoglobin: Molecular, Genetic and Clinical Aspects* (W. B. Saunders Co.) Philadelphia. Pa., 1986). This methemoglobin is physiologically inactive since it does not bind oxygen. Moreover, hemin can readily dissociate from the methemoglobin molecule because the bond between the iron atom and His93 (F8) is considerably weakened upon oxidation of the iron. Due to the insolubility of free hemin and apoglobin at physiological pH and temperature, hemin dissociation is essentially irreversible.

The affinity of the globins for heme is regulated through a combination of covalent, hydrophobic, electrostatic, and steric effects between the globins and bound hemin. The covalent bond between the His(F8) residue and the fifth coordination site of iron is an important force securing heme to the ferrous globins. However, after autooxidation this bond is considerably weakened, resulting in a faster rate of hemin dissociation from methemoglobin then from ferrous hemoglobin. Hydrophobic interactions between the methyl and vinyl substituents of the tetrapyrrole ring and the apolar regions of the globin make an important contribution to the retention of heme. Hydrogen bonding between His64(E7) and coordinated water helps to anchor heme in the globin. Salt bridges between polar amino acid residues at the surface of the globin and the heme-6- and heme-7-propionates also inhibit hemin loss. The heme-7-propionate forms hydrogen bonds with Lys(E10) in alpha and beta globin. The heme-6-propionate forms a salt bridge with His45(CE3) in alpha globin (Bunn, H. F., and Forget, B. G. (1986) Hemoglobin: Molecular, Genetic and Clinical Aspects, Chapter 16, pages 634–662, W.B. Saunders Company, Philadelphia, Pa.). The equivalent residue in the beta subunit, Ser44(CD3), is too far from the heme-6-propionate to form a similar interaction, and this lack of stabilization may contribute to the rapid rate of hemin loss from hemoglobin beta subunits.

The polypeptide chain between the C and E helices in alpha globins is 5 residues shorter than the equivalent region in beta globin, resulting in loss of helical secondary structure in this region of the protein (Kleinschmidt, T. & Squoros, J. *Hoppe-Seyler's Z. Biol. Chem*. 368, 579–615, 1987). Komiyama et al. (Komiyama, N., Shih, D., Looker, D., Tame, J., & Nagi, K. (1991) *Nature* 352, 49–51) examined the functional significance of the D helix in beta globins and its loss from alpha globins. No decrease in cooperativity or marked increase in $O_2$ affinity was observed. Komiyama et al. concluded that loss of the D-helix from alpha subunits was a functionally neutral mutation with respect to $O_2$ binding and assembly into a cooperative tetramer. However, this left unresolved the origin of the strong selective pressure to preserve a D-helix in the beta subunits of vertebrate hemoglobins.

Isolated hemoglobin subunits are highly unstable and lose hemin more readily than myoglobin. The resultant apohemoglobins are highly unstable at physiological pH and temperature. Because of the instability of hemoglobin subunits, myoglobin has been used as a model system to understand the principles of globin folding and stability. Apomyoglobin is considerably more stable, and its unfolding is a two step process (Hughson, F. M., Wright, P. E., and Baldwin, R. L. (1990) *Science* 249, 1544–1548). After myoglobin loses hemin, the native apomyoglobin denatures to a molten globule intermediate state resulting from unfolding of the B, C, and E helices. The remaining A, G, and H helices unfold during the transmission from the intermediate state to the completely unfolded state (Balastrieri, C., Colonna, G., Giovane, A., Irace, G., and Servillo, L., (1976) *Methods Enzymol*. 76, 72–77; Barrick and Baldwin, 1993; Hughson, F. M., Wright, P. E., and Baldwin, R. L. (1990) *Science* 249, 1544–1548; Hargrove, M. S., Krzywda, S. Wilkinson, A. J., Dou, Y., Ikeda-Saito, M., & Olson J. S. *Biochemistry* 33, 11767–11775, 1994).

Although myoglobin is a useful model system for the alpha and beta subunits of hemoglobin, the effects of muteginesis of key residues in myoglobin do not always have the same effects when introduced into the hemoglobin subunits. In fact, much has been learned from the differences. This point is best illustrated by the ligand binding studies of genetically engineered His(E7) and Val(E11) mutants of myoglobin, alpha subunits, and beta subunits (Carver, T. W., Rohlfs, R. J., Olson, J. S., Gibson, Q. H., Blackmore, R. S., Springer, B. A., and Sligar, S. G., *J. Biol. Chem*. 265: 20007–20020; Matthews, A. J., Rohlfs, R. J., Olson, J. S., Tame, J., Renaud, J., & Nagai, K. *J. Biol. Chem*. 264, 16573–16583, 1989; Mathews, A. J., Olson, J. S., Renaud, J.-P., Tame, J., & Nagai, K. (1991) *J. Biol. Chem*. 266, 21631–21639; Springer, B. A., Sligar, S. G., Olson, J. S., and Phillips, G. N., Jr. *Chem. Rev*. 94, 699–714, 1994). From a comparison of the observed effects on oxygen and carbon monoxide rate constants, a general rule has emerged. Myoglobin and R-state hemoglobin alpha subunits seem to have similar distal pocket structural and chemical mechanisms that discriminate against CO in favor of $O_2$. On the other hand, R-state beta subunits appear to have evolved somewhat different distal pocket mechanisms that accomplish the same physiological functions. In addition, hemoglobin interconverts between the R- and T-states. The alpha and beta subunits may have different structural and chemical mechanisms in each conformation. These observations raise the question as to whether or not mutations that have favorable effects on myoglobin stability will have similar effects in the hemoglobin subunits.

SUMMARY OF THE INVENTION

The present invention relates to method for reducing heme loss in a hemoglobin. The methods are accomplished by altering the amino acid sequence of a hemoglobin subunit. For example, the mutation can be seletected from any of the following:

(a) adding a D-helix region to an alpha subunit of said hemoglobin;

(b) altering the following amino acid residues in the beta subunit of said hemoglobin: Leu28(B10), Met32(B13), Thr38(C4), Phe41(C7), Phe42(CD1), Ser44(CD3), Phe45(CD4), the entire D-helix, His63(E7), Gly64(E8) Lys66(E10), Val67(E11), Ala70(E14), Leu88(F4), Leu91(F7), His92(F8), Leu96(FG3), Val98(FG5), Asn102(G4), Phe103(G5), Leu106(G8), Leu110(G12), Gly136(H14), Val137(H15), or Leu141(H19), wherein said beta subunit amino acid residues are identified by the native beta globin amino acid sequence of human hemoglobin; or (c) altering the following amino acid residues in the alpha subunit of the hemoglobin: Leu28(B10), Leu31(B13), Thr39(C4), Tyr42(C7), Phe43(CD1), His45(CD3), Phe46(CD4), His58(E7), Gly59(E8), Lys61(E10), Val62(E11), Ala65(E14), Leu83(F4), Leu86(F7), His87 (F8), Leu91(FG3), Val93(FG5), Asn97(G4), Phe98 (G5), Leu101(G8), Leu105(G12), Ser131(H14), Val132(H15), or Leu136(H19), wherein said alpha subunit amino acid residues are identified by the native alpha globin amino acid sequence of human hemoglobin.

In one embodiment, a D-helix region can be inserted into the alpha subunit with or without the removal of the D-helix from the beta subunit. Other mutations include the following substitutions in either the alpha or beta subunits; E11→Trp, E11→Leu, B10→Phe, B10→Trp, G8→Phe, G8→Trp, CD3→His, E11→Phe, F4→Phe, H14→Leu, B10→Val or B10→Ile.

The invention further relates to novel mutant hemoglobins that have higher affinity for heme and therefore reduce heme loss. Such mutant hemoglobins have beta globin mutations at Thr38(C4), Phe4(C7), D-helix, Gly64(E8) or Gly136 (H14) and/or alpha globin mutations at Thr39(C4), Gly59 (E8) or Ser131(H14).

DETAILED DESCRIPTION OF THE INVENTION

This invention relates to mutations in recombinant hemoglobin which confer significantly more resistance to the loss of heme relative to naturally occurring human hemoglobin and thereby increase the stability of the hemoglobins. Heme is the prosthetic group of hemoglobin, myoglobin, catalase, peroxidase, and cytochrome b. The heme is inserted in a cleft between the E and F helices. The heme iron is linked covalently to the imidazole nitrogen of the "proximal" F8 histidine. The distal E7 histidine and E11 valine appear to guard the access of oxygen to the heme pocket. The residues of the heme pocket include those residues that are on a nearest atom-to-nearest atom basis within 6 angstroms of the heme moiety, more preferably within 4 angstroms of the nearest heme atoms (Fermi, et al. (1984) *J. Mol. Biol.* 175: 159–174). The invention also relates to mutant hemoglobins containing mutations in the D helix, whether by addition or removal of the complete D helix from a given subunit or to multiple subunits, addition or removal of a portion of the D helix to a given subunit or to multiple subunits, or mutations in any of the residues comprising a naturally occurring or inserted D helix. In addition, the invention further relates to any mutation in any of the residues noted above, as well as double, triple and higher multiple mutations.

The mechanism by which the rate of heme loss from globin moieties can be modulated by alteration of the residues at the heme pocket and the D helix has been identified. Surprisingly, some mutations have been discovered which reduce only the rate of heme loss, but do not appear to change the oxygen binding and transport properties of the resultant mutant protein. Brief reviews of other effects of some distal pocket mutations on ligand binding to myoglobin and hemoglobin have been presented by Perutz (Perutz, M. F. (1989) *Trends Biochem. Sci.* 14: 42–44); Springer et al. (Springer, B. A., et al. (1994) *Chem. Rev.* 94: 699–714) and Mathews et al. (Mathews, A. J, et al., (1989) *J. Biol. Chem.* 264: 16573–16583) and the differences between myoglobin and hemoglobin have been noted in these and other publications.

Stabilizing amino acid replacements of the wild type human hemoglobin sequence are contemplated in the present invention within 6 Å, preferably within 4 Å of bound heme and at other secondary positions which affect heme loss in hemoglobins. These residues include: Leu28(B10), Met32(B13), Thr38(C4), Phe41(C7), Phe42(CD1), Ser44 (CD3), Phe45(CD4), the entire D-helix, His63(E7), Gly64 (E8) Lys66(E10), Val67(E11), Ala70(E14), Leu88(F4), Leu91(F7), His92(F8), Leu96(FG3), Val98(FG5), Asn102 (G4), Phe103(G5), Leu106(G8), Leu110(G12), Gly136 (H14), Val137(H15) and Leu141(H19) in β subunits and Leu29(B10), Leu31(B13), Thr39(C4), Tyr42(C7), Phe43 (CD1), His45(CD3), Phe46(CD4), His58(E7), Gly59(E8), Lys61(E10), Val62(E11), Ala65(E14), Leu83(F4), Leu86 (F7), His87(F8), Leu91(FG3), Val93(FG5), Asn97(G4), Phe98(G5), Leu101(G8), Leu105(G12), Ser131(H14), Val132(H15) and Leu136(H19) in α subunits. Some mutations of interest are, for example, CD3→His, E11→Phe, H14→Leu, B10→Val and B10→Ile mutations in either alpha, beta or both subunits and addition or removal of a D helix to either or both subunits. Note that mutations in equivalent positions in other mammalian or non-mammalian hemoglobins are also encompassed by this invention.

The factors governing heme binding to myoglobin and some related proteins including hemoglobin have been systemically examined (Hargrove et al., *Biochemistry*, 35: 11293–11299 (1996); Hargrove et al., *Biochemistry*, 35: 11300–11309 (1996); and Hargrove and Olson, *Biochemistry*, 35: 11310–11318 (1996), all incorporated herein by reference. The results of these studies show that heme association occurs at roughly the same rate for all proteins, about 100 $\mu M^{-1}s^{-1}$, and that heme affinity is governed solely by its rate of dissociation from the holoprotein. This result verifies the use of the assay described in Example 4 below as a way of quickly determining the affinity of recombinant hemoglobins for hemin. These studies also show that the stability of intact hemoglobin and myoglobin is governed exclusively by the affinity of the proteins for hemin and not by the stability of the apoprotein. Again, this result supports the premise that hemin affinity should be optimized to make a stable hemoglobin-based blood substitute and to obtain high expression yields in *E. coli*. Finally, the protein pocket which surrounds bound hemin was mutated systematically to determine the importance of individual amino acid residues in retaining heme in myoglobin. The corresponding residues in hemoglobin are listed in the paragraph above.

As noted above, the protein and DNA sequences of naturally occurring human hemoglobin are known. Any of the mutations described herein of the amino acids of the hemoglobin sequence can be accomplished by a number of methods that are known in the art. Mutation can occur at either the amino acid level by chemical modification of an amino acid or at the codon level by alteration of the nucleotide sequence that codes for a given amino acid. Substitution of an amino acid at any given position in a protein can be achieved by altering the codon that codes for that amino acid. This can be accomplished by site directed mutagenesis using, for example: (1) the Amersham technique (Amersham mutagenesis kit, Amersham. Inc., Cleveland, Ohio) based on the methods of Taylor et al., *Nucl. Acids Res.* (1985) 13: 8749–8764; Taylor et al., (1985) *Nucl. Acids Res.* 13: 8764–8785; Nakamaye and Eckstein, (1986) *Nucl. Acids Res.* 14: 9679–9698; and Dente et al., in *DNA Cloning*, Glover, Ed., IRL Press (1985) pages 791–802, (2) the Promega kit (Promega Inc., Madison, Wis.) or (3) the Biorad kit (Biorad Inc., Richmond, Calif.), based on the methods of Kunkel, (1985) *Proc. Natl. Acad. Sci. USA* 82: 488; Kunkel et al., (1987) *Meth. Enzymol.* 154: 367; Kunkel, U.S. Pat. No. 4,873,192. It can also be accomplished by other commercially available or non-commercial means which incorporate the technique of site-directed mutagenesis (using mutant oligonucleotides to achieve mutagenesis).

Site directed mutagenesis can also be accomplished using PCR based mutagenesis such as that described in Zhengbin et al., pages 205–207 in *PCR Methods and Applications*, Cold Spring Harbor Labratory Press, New York (1992); Jones and Howard, (1990) *BioTechniques* 8(2): 178; Jones and Howard, (1991) BioTechniques 10: 62–66. Site directed mutagenesis can also be accomplished using cassette mutagenesis with techniques that are known to those of skill in the art.

Mutants of hemoglobin are known and disclosed in PCT publication number WO88/09179, hereby incorporated by reference. Both the alpha and beta globin subunits have been sequenced (Hoffman and Nagai, U.S. Pat. No. 5,028,588, hereby incorporated by reference) and techniques for the mutation, expression and purification of the mutant recombinant hemoglobins have been described (Looker, D. et al. (1994) Expression of Recombinant Hemoglobin in *Escherichia coli* In: *Methods in Enzymology* 231: 364–374, S. O. Colowick, ed.; Academic Press, Inc.; Hoffman et al., WO 93/13645; Milne et al., WO 95/14038).

The mutations described herein are also useful for improving the expression yield of hemoglobin in recombinant systems. Increasing hemin affinity can contribute to increased protein expression yields. Without being bound by theory, stabilization of the holoprotein may allow the proteins to exist longer in the cell after expression. In addition, some mutations that are described herein may result in stabilized apoglobins (the globin without the heme). Without being bound by theory, if the mutant apoglobin is more stable than the respective wild type apoglobin, it may exist longer in the cell after expression. Therefore, it will have a longer time in the cell to bind with the heme and ultimately, combine with other subunits to form the hemoglobin tetramer.

Accordingly, the present invention also provides methods for enhanced production of hemoglobin from recombinant systems by improved expression of mutant hemoglobins. Such methods are accomplished by obtaining nucleic acid sequence coding for a mutant alpha subunit, beta subunit or mutants of both the alpha and beta globins of the instant invention. Such nucleic acid sequences can then be introduced into any suitable expression system by any suitable means. Heterologous proteins have been expressed in a number of biological expression systems, such as insect cells, plant cells, transgenic cells, yeast systems and bacterial systems. Thus, any suitable biological protein expression system can be utilized to produce large quantities of recombinant hemoglobin. Indeed, hemoglobin has been expressed in a number of biological systems, including bacteria (Hoffman et al., WO 90/13645), yeast (De Angelo et al., WO 93/08831 and WO 91/16349; Hoffman et al., WO 90/13645) and transgenic mammals (Logan et al., WO 92/22646; Townes, T. M and McCune, S. L., WO 92/11283).

The average lifetime of a red blood cell is ~160 days (Vandegriff, K. D. (1992) *Biotechnology and Genetic Engineering Reviews* 10, 403–453). Methemoglobin is maintained at low levels in an RBC due to the presence of enzymatic reducing systems. However, hemoglobin that is not sequestered in a red blood cell is oxidized within ~2–3 days. In vivo, methemoglobin production may occur even faster in the presence of oxidants. A lower rate of hemin loss could prevent rapid release of the prosthetic group and possible saturation of the serum albumin/apohemopexin scavenging systems. In addition, lower heme loss may allow opportunities for re-reduction of an oxidized heme, thus increasing the amount of functional hemoglobin in a system. Free heme in vivo promotes oxidative and peroxidative membrane and protein damage which ultimately causes red blood cell lysis and damage to vascular tissue (Vincent, S. H. *Semin Hematol.* 26, 105–113, 1989; Vandegriff, K. D. (1992) *Biotechnology and Genetic Engineering Reviews* 10, 403–453 and Vandegriff, K. D. (1995) in *Blood Substitutes: Physiological Basis of Efficacy* (Birkhauser, Boston) pp. 105–131). After red blood cell lysis, apohemopexin and serum albumin bind free hemin, transferrin binds free iron, and haptoglobins bind the denatured apoglobins. These complexes are then transported to the liver, spleen, and bone marrow for degradation or reabsorption. These systems could become quickly saturated if breakdown of exogenous cell-free hemoglobin occurred rapidly. Thus mutants of hemoglobin with reduced rates of hemin loss can be useful for reducing heme exposure from hemoglobin-based oxygen carriers. Lastly, in the presence of exogenous reduction systems, increased hemin affinity can increase hemoglobin shelf life and retention time in the blood stream by increasing the chance for re-reduction of the heme after oxidation by increasing the residence time of the heme in the globin.

The heme-loss resistant mutant hemoglobins of the present invention can be used for the formulation of pharmaceutical or non-pharmaceutical compositions. Suitable pharmaceutical compositions for the mutant recombinant hemoglobins of the invention are described in co-pending applications of Milne, et al., WO 95/14038 and Gerber et al., PCT/US95/10232. Pharmaceutical compositions of the invention can be useful for, for example, subcutaneous, intravenous, or intramuscular injection, topical or oral administration, large volume parenteral solutions useful as blood substitutes, etc. Pharmaceutical compositions of the invention can be administered by any conventional means such as by oral or aerosol administration, by transdermal or mucus membrane adsorption, or by injection. Non-pharmaceutical compositions of the invention can be used as, for example, reference standards for analytical instrumentation needing such reference standards, reagent solutions, control of gas content of cell cultures, for example by in vitro delivery of oxygen to a cell culture, and removal of oxygen from solutions.

In one embodiment, the compositions can be formulated for use in therapeutic applications. For example, the formulations of the present invention can be used in compositions useful as substitutes for red blood cells in any application that red blood cells are used. Such compositions of the instant invention formulated as red blood cell substitutes can be used for the treatment of hemorrhages, traumas and surgeries where blood volume is lost and both fluid volume and oxygen carrying capacity must be replaced. Moreover, because the compositions of the instant invention can be made pharmaceutically acceptable, the formulations of the instant invention can be used not only as blood substitutes that deliver oxygen but also as simple volume expanders that provide oncotic pressure due to the presence of the large hemoglobin protein molecule.

A typical dose of hemoglobin as blood substitute is from 10 mg to 5 grams or more of extracellular hemoglobin per kilogram of patient body weight. Thus, a typical dose for a human patient might be from a few grams to over 350 grams. It will be appreciated that the unit content of active ingredients contained in an individual dose of each dosage form need not in itself constitute an effective amount since the necessary effective amount could be reached by administration of a plurality of administrations as injections, etc. The selection of dosage depends upon the dosage form utilized, the condition being treated, and the particular purpose to be achieved according to the determination of the ordinarily skilled artisan in the field.

Administration of extracellular hemoglobin can occur for a period of seconds to hours depending on the purpose of the hemoglobin usage. For example, a blood delivery vehicle, the usual time course of administration is as rapid as possible. Typical infusion rates for hemoglobin solutions as blood replacements can be from about 100 ml to 3000 ml/hour.

In a further embodiment, the compositions of the instant invention can be used to treat anemia, both by providing additional oxygen carrying capacity in a patient that is suffering from anemia, and by stimulating hematopoiesis. When used to stimulate hematopoiesis, administration rates can be slow because the dosage of hemoglobin is much smaller than dosages that can be required to treat hemorrhage.

In addition, because the distribution of the hemoglobin in the vasculature is not limited by the size of the red blood cells, the hemoglobin of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation and the like. Because of this broad distribution in the body, the hemoglobins of the instant invention may also be used to deliver drugs and for in vivo imaging.

The compositions of the instant invention can also be used as replacement for blood that is removed during surgical procedures where the patient's blood is removed and saved for reinfusion at the end of surgery or during recovery (acute normovolemic hemodilution or hemoaugmentation).

Because the hemoglobin of the instant invention can bind nitric oxide and other non-oxygen ligands as well as oxygen, the formulations of the instant invention are also useful for the binding or delivery of nitric oxide or non-oxygen ligands. These non-oxygen ligands can be bound or delivered both in vivo or in vitro. For example, the hemoglobin mutants of the instant invention can be used to remove excess nitric oxide from a living system. Excess nitric oxide has been implicated in conditions ranging from hypotension to septic shock. Likewise, nitric oxide or other non-oxygen ligands can be delivered to a system to alleviate a disease condition. For example, nitric oxide could be delivered to the vasculature to treat hypertension.

In the same manner, high heme affinity mutants can be used to scavenge excess heme from both in vivo and in vitro systems. Excess heme can be scavenged by administering an effective amount of such high heme affinity mutants to reduced excess heme from the system of interest. The apoprotein (the hemoglobin protein without the prosthetic heme groups), the apoglobin (the individual subunits without the prosthetic heme groups), the holoprotein (the hemoglobin protein with prosthetic groups) or the hologlobins (the individual subunits with the heme groups) can be administered. Excess heme in vivo has been associated with, for example, pathological states such as hemolytic anemias of any origin, porphyrias and hemochromatosis. Such disease states can be treated by administration of an effective amount of one or more high heme affinity hemoglobin mutants, such as those described herein.

The composition of the present invention can also be used for a number of in vitro applications. For example, the delivery of oxygen by compositions of the instant invention can be used for the enhancement of cell growth in cell culture by maintaining oxygen levels in vitro. Moreover, the hemoglobins of the instant invention can be used to remove oxygen from solutions requiring the removal of oxygen, removal of heme from solutions requiring the removal of heme, and as reference standards for analytical assays and instrumentation.

EXAMPLES

The following examples are provided by way of describing specific embodiments of the present invention without intending to limit the scope of the invention in any way.

Example 1

Preparation of Recombinant Hemoglobins

The recombinant human hemoglobin gene, pSGE0.0E4, was created according to the methods of Hoffman et al. (Hoffman, S. J., Looker, D. L., Roehrich, J. M., Cozar, P. E., Durfee, S. L., Tedesco, S. L., & Stetler, J. L. *Proc. Natl. Acad. Sci U.S.A.* 87, 8251–8525, 1990). It consists of one alpha globin and one beta globin cistron expressed from a single operon under control of the pTac promoter. Each gene bad been engineered to maximize protein yields by incorporating *E. coli* biased codons, efficient ribosomal binding sites, and optimal translational start and stop codons. Each cistron also had its N-terminal Val coding sequence deleted and replaced with the bacterial translational start sequence which codes for Met. The hemoglobin gene was placed into the pKK223-3 expression vector (Pharmacia, Piscataway, N.J.) and labeled pSGE0:0E4. The pKK223-3 vector, however, does not contain an F1 origin of replication to create single stranded DNA for oligonucleotide site directed mutagenesis. For this reason, the pBluescriptII KS+ plasmid (Pharmacia, Piscataway, N.J.) was used as the mutagenic vector. The alpha and beta genes were individually subcloned into separate vectors, mutagenized, and subcloned back into the pSGE0.0E4 expression vector. The hemoglobin B10 and CD3 mutants were constructed using the Amersham Sculptor (Cleveland, Ohio) mutagenesis kit according to Taylor et al. (Taylor, J. W., Ott, J., and Eckstein, F., (1985) *Nucl. Acids Res.* 13, 8764–8785). The hemoglobin alpha(0.0)beta(–D) and alpha(+D)beta(0.0) mutants were created using cassette mutagenesis (Komiyama, N., Shih, D., Looker, D., Tame, J., & Nagai, K. *Nature* 352, 49–51, 1991). The D helix from human beta globin was removed by deleting residues Thr50-Pro-Asp-Ala-Val54. This same set of residues was inserted into alpha globin starting at position 49. The corresponding mutants were designated beta(–D) and alpha(+D), respectively, and two hemoglobin hybrids were made, alpha(wild-type)beta(–D) and alpha(+D)beta (wild-type). Wild-type refers to subunits which are identical to the native proteins except for V1M substitutions to facilitate expression in *E. coli*.

The recombinant hemoglobins were expressed and purified by the following methods. A 14 liter fermentor was used to grow the JM109 *E. coli* cells containing the wild type or mutant hemoglobin vectors to an $OD_{600}$ of 2.0–3.0 using terrific broth (Sambrook, J., Fritsch, E. F., and Maniatis, T. (1989) *Molecular Cloning: A Laboratory Manual*. Cold Spring Harbor Laboratory, Cold Spring Harbor, N.Y.) and 0.017 M $KH_2PO_4$/0.072 M $K_2HPO_4$ buffer pH 7.0 at 30° C. At this time, hemoglobin expression was induced with isopropyl-β-thiogalactopryanoside (IPTG) (300 mM).

Exogenous heme, predissolved in 0.1 M NaOH, was also added to a final concentration of 30 mg/ml. 667 The cells were grown for an additional 4 hours, harvested by centrifugation, weighed, and then frozen at −70° C. Freezing appears to aid in cell lysis. The next day the cells were thawed at room temperature until ice crystals were still present. The cells were then resuspended by blending for 2 minutes in lysis buffer (40 mM tris base/1 mM benzamidine pH 8.0; 3 mls/1 g cell paste). Lysozyme, predissolved in lysis buffer, was added to 1 mg/1 g cell paste and incubated for 20 minutes at 10° C. After brief blending, Mg/Mn was added to a final concentration of 0.01 M/0.001M prior to the addition of DNase 20 ug/ml lysate. The lysate was then incubated for another 20 minutes at 10° C. To precipitate the DNA, 10% polyethyleneimine was added slowly to a final concentration of 0.05% and the lysate was stirred for 15 minutes prior to being centrifuged for 20 minutes at 14,000×g in a Beckman J20 rotor. The supernatant was then concentrated using a MINITAN high resolution tangential flow filtration system (Millipore, Inc., Bedford, Mass.) and its conductivity was reduced to that of the first column by adding distilled water. The pH was brought to pH 7.4 with 0.1 M HCl.

The purification of the recombinant hemoglobins was achieved using three chromatographic columns. The first column contained the anionic exchanger, fast flow Q SEPHAROSE (Sigma Chemical Company, St. Louis, Mo.), equilibrated in 20.0 mM tris-Cl/0.1 mM triethylaminetetraacetic acid at pH 7.4. The first column was designed to let hemoglobin pass through and to bind all proteins with isoelectric points less than 7.4. The second column was packed with fast flow Q SEPHAROSE and equilibrated in 20.0 mM tris-Cl pH 8.5. Hemoglobin is anionic at this pH and bound to the column while all proteins with isoelectric points greater than 8.5 passed through the column. Hemoglobin protein was eluted with a pH gradient of 200 ml 20.0 mM tris-Cl pH 8.5 to 20.0 mM tris-Cl pH 7.0. The last column contained the cationic exchanger, fast flow S SEPHAROSE (Sigma Chemical Company, St. Louis, Mo.), equilibrated in 20.0 mM $Na_2HPO_4$, pH 6.8. Hemoglobin is positively charged at this pH and bound tightly to the column. Hemoglobin was eluted using a pH gradient of 200 ml 20.0 mM $Na_2HPO_4$ at pH 7.0 to 20.0 mM $Na_2HPO_4$ at pH 8.0. The final eluent was concentrated to 1–2 mM heme and stored in liquid nitrogen.

Example 2

Measurement of Rate and Equilibrium Constants for $O_2$ and CO Binding

All rate constants were measured under pseudo-first order conditions in which the ligand concentration was much greater than the heme concentration. All hemoglobin reactions were conducted in 0.1 M bis-tris/0.1 M KCl/1.0 mM EDTA pH 7.0 at 20° C. The hemoglobin association and dissociation time courses are biphasic, with the fast phase being assigned to the beta subunits and the slow phase to the alpha subunits (Mathews, A. J., Rohlfs, R. J., Olson, J. S., Tame, J., Renaud, J., & Nagai, K. (1989) *J. Biol. Chem.* 264, 16573–16583). Thus, the hemoglobin time courses were fitted to a two exponential expression with equal amplitudes.

$O_2$ and CO dissociation rate constants, $k_{O2}$ and $k_{CO}$, for R-state hemoglobins were determined by replacement reactions as described by Mathews et al., (Matthews, A. J., Rohlfs, R. J., Olson, J. S., Tame, J., Renaud, J., & Nagai, K. (1989) *J. Biol. Chem.* 264, 16573–16593). $k_{O2}$ was determined by measuring the rate constant for $O_2$ displacement by CO as a function of the ratio of $[O_2]/[CO]$:

$$r_{obs} = \frac{k_{O2}}{1 + \frac{k_{O2}^0[O_2]}{k_{CO}^0[CO]}}$$

Were $r_{obs}$ is the observed replacement rate, $k_{O2}'$ and $k_{CO}'$ are the oxygen and carbon monoxide association rate constants, and $k_{O2}$ is the true oxygen dissociation rate constant. $k_{CO}$ was determined by displacing bound CO with NO. Since $k_{NO}' \ggg k_{CO}'$, the observed rate constant reduces to: $r_{obs} = K_{CO}$ The ligand association rate constant for R-state hemoglobin were determined as described by Matthews et al., (Mathews, A. J., Rohlfs, R. J., Olson, J. S., Tame, J., Renaud, J., & Nagai, K. (1989) *J. Biol. Chem.* 264, 16573–16583). The R-state hemoglobin carbon monoxide association rate constants, $k_{CO}'$, were determined by flash photolysis using a millisecond apparatus employing two photographic strobes (Sunpack Auto 544, Sunpack Corporation, Woodside, N.Y.). This apparatus was interfaced to a 3820 OLIS DATA collection system (On-Line-Systems, Inc., Bogart, Ga.). The R-state hemoglobin oxygen association rate constants, $k_{O2}'$, were determined by using a 300 ns laser photolysis system (Phase R 2100B, Phase-R Corporation, New Durham, N.H.; equivalent available from Candela Corporation) interfaced to a Tektronics digital oscilloscope model 2430 (Tektronics, Inc., Beaverton, Oreg.). The R-state hemoglobin conformation was retained by only measuring the last step in ligand binding, $(Hb_4X_3 + X \rightarrow HB_4X_4)$. This was accomplished by measuring the rates of ligand binding at 10% photolysis using neutral density filters to reduce the absorbance change to 1/10 of the total absorbance change expected for binding to fully deoxygenated hemoglobin. For simple bimolecular reactions (i.e., globin+ligand) the dependence of the observed rate on ligand concentration is given by: $r_{obs} = k_x^C [X] + k_x$ Example 3

Measurement of Autooxidation Rates

Hemoglobin oxidation rates were determined as described by Zhang et al. (Zhang, L. Levy, A., and Rifkind, J. M. (1991) *J. Biol. Chem.* 266, 24698–24701). Since hemoglobin oxidation at pH 7.0 is relatively slow (2–3 days), most reactions were carried in 0.1 m $KPO_4$, 1 mM EDTA at pH 6.0 to speed up the reaction and obtain more accurate rate constants. The reactions were performed in a 1 ml cuvette containing ~6.0 mM heme protein, 3 mmol/mol heme of catalase, and 3 mmol/mol heme superoxide. Hemoglobin autooxidation time courses were fitted to a single exponential expression at both pH 6 and 7.4, 37° C.

Example 4

Measurement of Hemin Dissociation Rates

Time courses for the dissociation of hemin were measured using the H64Y/V68F apomyoglobin reagent developed by Hargrove et al., (Hargrove, M. S., Singleton, E. W., Quillin, M. L., Mathews, A. J., Ortiz, L. A., Phillips, G. N., Jr., & Olson, J. S. (1994) *J. Biol. Chem.* 269, 4207–4214). The reactions were measured at 37° C. in 0.15 M $KPO_4$/0.45M sucrose at either pH 5.0 (sodium acetate) or pH 7 (potassium phosphate). The reactions contained ~6.0 $\mu$M (unless otherwise specified) methemoglobin in the presence of excess H64Y/V68F apomyoglobin, generally 12.0–24.0 $\mu$M. The H64Y/V68F myoglobin heme loss reagent has an unusual absorption spectra giving rise to a green color. The reaction can be described by:

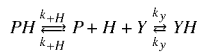

$$PH \underset{k_{+H}}{\overset{k_{+H}}{\rightleftharpoons}} P + H + Y \underset{k_y}{\overset{k_y}{\rightleftharpoons}} YH$$

where P represents the heme containing globin of interest, H is equal to heme, and Y is the H64Y/V68F mutant apomyoglobin. When [P] and/or [Y] are >>[H], the d[H]/dt~0, and the rate of hemin dissociation, $k_{-H}$, is given by:

$$\frac{k_{+H} + k_y \left( \frac{k_H[P]}{k_y[Y]} \right)}{1 - \frac{k_H[P]}{k_y[Y]}}$$

which reduces to $r_{obs}=k_{-M}$ when [Y]>>[P] (Hargrove, M. S., Singleton, E. W., Quillin, M. L., Mathews, A. J., Ortiz, L. A., Phillips, G. N., Jr. & Olson, J. S., (1994a) *J. Biol. Chem.* 269, 4207–4214).

The total reaction volumes were 800 µL and measured in a 1.0 ml cuvette with a 1.0 cm path length. A six cell Shimadzu 2101 UV-Vis specotometer (Shimadzu Scientific Instruments, Columbia, Md.) connected to a CPS-260 temperature controller was used to collected the absorbance changes at the specified time intervals. The hemoglobin of interest was first oxidized with ferricyanide. One grain of ferricyanide was added to about 50 µL of 1 mM oxy- or carbonmonoxyhemoglobin. The protein solution was then run down a G25 SEPHADEX (Sigma Chemical Company, St. Louis, Mo.) column equilibrated in 10.0 mM potassium phosphate pH 7 at room temperature. The buffer and H64Y/V68F apomyoglobin reagent were equilibrated at the specified temperature in the spectrophotometer prior to the addition of the ferric protein of interest. Time courses were fitted to single or double exponential expressions using the IGOR Pro analysis program (Wavemetrics, Inc., Lake Oswego, Oreg.). Hemoglobin time courses were biphasic with hemin loss from the alpha and beta subunits showing equal absorbance changes. The fast phase of hemin loss is due to hemin loss from the beta subunits and the slow phase to hemin loss from alpha subunits. Hemoglobin time courses were fitted to a two exponential expression with equal amplitudes. Occasionally, the time courses were fit to a three exponential expression with the third phase representing slow absorbance drift caused by protein denaturation.

Example 5

Hemin Loss Rates of Hemoglobin D Helix Mutants

Hemoglobin D-helix mutants were expressed and purified as described in Example 1. Ligand binding was measured and described in Example 2. As shown in Table 1, removal of the D helix from beta subunits or addition of this 5 residue sequence to alpha subunits had only a moderate effect on $O_2$ and CO binding in R-state hemoglobin. The biggest change was observed for the double mutant, alpha(+D)beta(–D), for which the alpha and beta $K_{O2}$ and $K_{CO}$ values were 2- and 4-fold less, respectively, than the corresponding constants for wild-type hemoglobin.

Hemin dissociation was measured as described in Example 4. Removal of the D-helix from beta subunits had a significant effect on the rate of hemin dissociation. In the alpha(wild-type)beta(–D) hybrid, the rate of hemin loss from beta subunits increased greater than 3-fold and the rate from alpha subunits increased 8-fold (Table 2). The alpha (wild type)beta(–D) apoglobin was also very unstable and tended to precipitate during the hemin loss assay, making precise measurement of the slow phase difficult. Without being bound by theory, these results suggest that removal of the D helix increased the rate of hemin loss and caused unfolding of the beta subunit. The remaining holo alpha subunits in this partially denatured semi-globin were destabilized due to loss of interactions with native beta globin partners and lost hemin rapidly. Isolated alpha subunits lost hemin much more rapidly than when they were coupled to beta subunits in hemoglobin (~15–20 $h^{-1}$ versus 0.3 to 0.5 $h^{-1}$, respectively, at pH 7, 37° C.). In addition, the expression yield of alpha(wild-type)beta(–D) hemoglobin was much lower than that of wild-type and any of the other D-helix hemoglobin mutants, indicating an unstable apoglobin and poor heme binding.

TABLE 1

R-State Hemoglobin Subunit Rate and Equilibrium Constants for Oxygen and Carbon Monoxide Binding at 20° C. in 0.1 M Bix-Tris, 0.1 M KCl, and 1.0 mM EDTA pH 7.0

| Hemoglobin | $k'_{O2}$ $\mu M^{-1} s^{-1}$ | | $k_{O2}$ $s^{-1}$ | | $K_{O2}$ $\mu M^{-1}$ | | $k'_{CO}$ $\mu m^{-1} s^{-1}$ | | $k_{CO}$ $s^{-1}$ | | $K_{CO}$ $\mu M^{-1}$ | |
|---|---|---|---|---|---|---|---|---|---|---|---|---|
| | α | β | α | β | α | β | α | β | α | β | α | β |
| $\alpha_{(native)}\beta_{(native)}$ | 23 | 79 | 11 | 28 | 2.0 | 2.8 | 2.7 | 7.6 | 0.0089 | 0.011 | 300 | 690 |
| $\alpha_{(wt)}\beta_{(wt)}$ | 19 | 74 | 15 | 47 | 1.3 | 1.6 | 2.2 | 5.9 | 0.0086 | 0.010 | 260 | 590 |
| $\alpha_{(+D)}\beta_{(wt)}$ | 24 | 75 | 21 | 43 | 1.1 | 1.7 | 1.7 | 5.1 | 0.0230 | 0.013 | 74 | 390 |
| $\alpha_{(wt)}\beta_{(-D)}$ | 21 | 110 | 14 | 58 | 1.5 | 1.8 | 2.3 | 7.5 | 0.0081 | 0.017 | 280 | 440 |
| $\alpha_{(+D)}\beta_{(-D)}$ | 13 | 25 | 13 | 41 | 1.0 | 0.61 | 1.7 | 5.0 | 0.014 | 0.027 | 120 | 180 |

Insertion of the D helix into alpha globin had no effect on the rates of hemin loss when wild-type beta subunits were present in the hemoglobin hybrid. However, the alpha(+D)beta(–D) double mutant was significantly more resistant to hemin loss and precipitation than alpha(wild-type)beta(–D) (Table 2). In addition, the expression yield of alpha(+D)beta (wild-type) hemoglobin was approximately 3-fold greater than alpha(wild-type)beta(wild-type), both of which were much greater than that of the unstable alpha(wild-type)beta (–D) mutant. Thus, although addition of an alpha D-helix did not decrease the rate of hemin loss from hemoglobin, it did stabilize the alpha apoglobin structure. Without being bound by theory, stabilized alpha apoglobins may explain the enhanced expression yields of the alpha(+D)beta(wild-type) hybrid and low rates of hemin loss from the alpha(+D)beta(–D) hybrid compared to the alpha(wild-type)beta(–D) mutant.

Overall rates of autooxidation of the recombinant hemoglobins are also listed in Table 2. These data show that removing the D-helix from beta subunits also enhances hemoglobin autooxidation ~5-fold at low pH.

The results in Table 1 show that the D-helix in hemoglobin beta subunits is required for inhibition of hemin loss and autooxidation, even though it plays little role in regulating oxygen binding. Addition of a D-helix to alpha subunits caused no change in the rate of hemin loss from hemoglobin with wild-type beta subunits. On the other hand, the rate of hemin loss from alpha subunits increased almost 10-fold when paired with beta(-D) subunits, and the presence of an alpha D-helix resulted in a marked decrease in the rate of hemin loss from the alpha(+D)beta(-D) hybrid. When alpha subunits were completely separated from beta subunits, the rate of hemin dissociation increased ~100-fold compared to that observed for alpha subunits in either dimers or tetramers.

globin ($k_{-H}$) are presented in Table 4. The alpha His45(CE3)→Arg mutation had no effect on hemin dissociation from either subunit. Likewise, the beta Ser44(CD3)→Arg and Lys substitutions appear to be conservative with respect to hemin loss. On the other hand, Table 4 shows that the beta Ser44(CD3)→His mutation causes a significant and specific 3–5-fold reduction in the rate of hemin loss from the beta subunit.

TABLE 3

R-State hemoglobin alpha and beta subunit rate and equilibrium constants for oxygen and carbon monoxide binding at 20° C. in 0.1 M bis-tris, 1.0 mM EDTA pH 7.0.

| Hemoglobin | $k'_{O2}$ $\mu M^{-1}s^{-1}$ | | $k_{O2}$ $s^{-1}$ | | $K_{O2}$ $\mu M^{-1}$ | | $k'_{CO}$ $\mu m^{-1}s^{-1}$ | | $k_{CO}$ $s^{-1}$ | | $K_{CO}$ $\mu M^{-1}$ | |
|---|---|---|---|---|---|---|---|---|---|---|---|---|
| | α | β | α | β | α | β | α | β | α | β | α | β |
| $\alpha_{(wt)}\beta_{(wt)}$ | 16 | 79 | 14 | 33 | 1.1 | 2.4 | 2.2 | 5.2 | 0.0054 | 0.013 | 410 | 400 |
| $\alpha_{(wt)}\beta_{(CD3H)}$ | 19 | 82 | 16 | 24 | 1.2 | 3.8 | 2.3 | 6.7 | 0.0051 | 0.013 | 450 | 520 |
| $\alpha_{(wt)}\beta_{(CD3K)}$ | 24 | 76 | 11 | 29 | 2.2 | 2.6 | 1.9 | 4.4 | 0.011 | 0.014 | 170 | 310 |
| $\alpha_{(wt)}\beta_{(-CD38)}$ | 25 | 97 | 13 | 30 | 2.0 | 2.9 | 2.5 | 5.7 | 0.011 | 0.017 | 230 | 330 |
| $\alpha_{(CD3R)}\beta_{(wt)}$ | 26 | 105 | 15 | 40 | 1.7 | 2.6 | 3.7 | 11 | 0.004 | 0.014 | 930 | 790 |

TABLE 2

Rate constants for hemin loss and autooxidation of D-helix hemoglobin mutants at 37° C. and 3–6 μM heme. Hemin dissociation was measured at pH 7, whereas oxidation was measured at pH 5.

| Hemoglobin | α $k_{-H}$ $h^{-1}$ | β $k_{-H}$ $h^{-1}$ | $k_{ox}$ $h^{-1}$ |
|---|---|---|---|
| $\alpha_{(wt)}\beta_{(wt)}$ | 0.42 | 16 | 0.90 |
| $\alpha_{(+D)}\beta_{(wt)}$ | 0.44 | 15 | 0.84 |
| $\alpha_{(wt)}\beta_{(-D)}$ | 3.3 | 48 | 5.4 |
| $\alpha_{(+D)}\beta_{(-D)}$ | 1.0 | 33 | 3.0 |

Example 6

Alpha(CE3) and Beta(CD3) Mutant Hemoglobins

Alpha CE3 and Beta CD3 mutants were constructed, expressed and purified as described in Example 1. Ligand binding, autooxidation rates and hemin dissociation rates were measured as described in Examples 2, 3 and 4 respectively. The rate and equilibrium parameters for $O_2$ and CO binding to recombinant R-state hemoglobins are presented in Table 3. The alpha His45(CE3)→Arg, and beta Ser44 (CD3)→His, Arg, and Lys replacements cause little change in $K_{O2}$ and $K_{CO}$, respectively. The most significant effects were small (~2-fold) increases in $K_{CO}$ for the alpha and beta subunits of alpha(Arg44CE3)beta(wt). Autooxidation rate constants for these hemoglobin mutants were determined at pH 6 (Table 4). The time courses were monophasic at this pH despite the presence of two types of subunits. The alpha His45(CE3)→Arg and beta Ser44(CD3)→Arg, Lys, and His substitutions had only modest effects on autooxidation. The alpha Arg45(CE3) and beta Arg44(CD3) mutants showed the largest effects, ~3-fold increases in $k_{O2}$ as compared to that for wild type oxyhemoglobin. In contrast to what is observed in myoglobin, increasing the basicity of alpha 45(CE3) and beta 44(CD3) increased their rates of autooxidation.

The fitted values for time courses for hemin dissociation from wild type and CD3 or CE3 mutants of human hemo-

TABLE 4

Hemin Loss and autooxidation rate constants for the alpha(CE3) and beta (CD3) hemoglobin mutants. Hemin loss rates were measured at 6.0 μM heme concentration in 0.15M potassium phosphate, 0.45M sucrose, pH 7, and 37° C. Oxidation rates were measured at 6.0 μM heme concentration in 0.1M potassium phosphate, 0.3 mM EDTA, pH 6, and 37° C.

| Hemoglobin | α $k_{-H}$ (hr$^{-1}$) | β $k_{-H}$ (hr$^{-1}$) | $k_{ox}$ (hr$^{-1}$) |
|---|---|---|---|
| $\alpha_{(wt)}\beta_{(wt)}$ | 0.50 | 16 | 0.087 |
| $\alpha_{(wt)}\beta_{(CD3H)}$ | 0.54 | 5.0 | 0.18 |
| $\alpha_{(wt)}\beta_{(CD3K)}$ | 0.70 | 14 | 0.11 |
| $\alpha_{(wt)}\beta_{(CD3R)}$ | 0.80 | 19 | 0.28 |
| $\alpha_{(CE3R)}\beta_{(wt)}$ | 0.60 | 21 | 0.26 |

The relative rates of hemin dissociation from methemoglobin are tetramers<dimers<<monomers. Aggregation into $alpha_1beta_1$ dimers caused a marked decrease in $k_{-H}$ for alpha subunits, but had only a small effect on beta subunits which lose hemin quickly (~15 h$^{-1}$). Formation of the $alpha_1beta_2$ interface in tetramers caused a 10-fold decrease in $k_{-H}$ for beta subunits. The beta subunit of alpha(wt)beta (His44CD3) lost hemin 3- to 5-fold slower than the beta subunit of wild type hemoglobin at both very low and very high heme concentrations (Table 5). The fitted values of $k_{-H}^{dimer}$ and $k_{-H}^{tetramer}$ were 10 and 0.4 h$^{-1}$ for beta His44(CD3) subunits, and 30 and 2 h$^{-1}$ for the wild type beta subunits, respectively. The alpha subunits showed a $k_{-H}$ value of ~0.5 h$^{-1}$ for both dimers and tetramers, regardless of the presence of absence of the mutation in beta subunits. The fitted value of the equilibrium constant for tetramer dissociation into dimers for the mutant hemoglobin at ~6 μM heme was nearly identical to that obtained for fits to wild type hemoglobin at ~8 mM heme in 0.45 M sucrose/0.15 M potassium phospate, pH 7, and 37° C.

TABLE 5

Rate of hemin loss for the alpha and beta subunits of native, wild type, and the beta His44(CD3) mutant hemoglobin as dimers at low protein concentration (1 μM) and tetramers at high protein concentration (600 μM). Reactions were measured in 0.45M sucrose, 0.15M potassium phosphate, pH 7, and 37° C.

| Hemoglobin Subunit | $k_{-H}^{dimer}$ (h$^{-1}$) | $k_{-H}^{tetramer}$ (h$^{-1}$) |
| --- | --- | --- |
| $\alpha_{(native)}$ | 0.50 | 0.50 |
| $\alpha_{(wt)}$ | 0.50 | 0.50 |
| $\beta_{(native)}$ | 15 | 1.7 |
| $\beta_{(wt)}$ | 30 | 1.9 |
| $\beta_{(His44CD3)}$ | 11 | 0.40 |

Example 7

Alpha Leu29(B10) and Beta Leu28(B10) Mutant Hemoglobins

Alpha Leu29(B10)→Ala, Val, and Ile, and beta Leu28 (B10)→Ala, Val, Ile, and Trp substitutions were constructed, expressed and purified as described in Example 1. Ligand binding, autooxidation rates and hemin dissociation rates were measured as described in Examples 2, 3 and 4 respectively. The Leu(B10)→Phe mutation was constructed, expressed and purified according to the methods described in co-pending application 08/381,175, filed Jan. 30, 1995, herein incorporated by reference.

Table 6 lists the measured rate and equilibrium constants for O2 and CO binding to alpha and beta subunits within R-state hemoglobins. The Leu(B10)→Val mutation had little effect on $K_{O2}$ for all three globins. The Leu29(B10) →Val mutation did cause a dramatic 25-fold decrease in $K_{CO}$ for alpha globin due to a large 9-fold decrease in k'$_{CO}$ and a 3-fold increase in $k_{CO}$. In contrast, this mutation had little effect on $K_{CO}$ in beta globin. The Leu(B10)→Ile substitution decreased both $k_{O2}$' and $k_{O2}$ in α globin, with little change in oxygen affinity. Interestingly, the Ile28(B10) in β globin had a much larger effect on oxygen dissociation decreasing $k_{O2}$ and $K_{O2}$ ~7-fold and ~3-fold, respectively. Again, the most dramatic effects were observed for $K_{CO}$.

Increasing the size of Leu(B10) to Phe decreased k'$_{O2}$ 30-fold and 10-fold for R-state alpha and beta subunits, respectively (Table 6). The Phe(B10) mutation also slowed $k_{O2}$ in each globin, but by markedly different degrees. The Leu(B10)→Phe replacement decreased $k_{O2}$ 40-, and 3-fold for R-state alpha subunits, and R-state beta subunits, respectively, as compared to the wild type values. As a result, $K_{O2}$ increased ~3-fold for R-state alpha subunits, whereas $K_{O2}$ decreases ~2-fold for R-state beta subunits. The Leu(B10)→Phe replacements also affected $K_{CO}$ differently in each globin. CO affinity decreased a dramatic 60-fold for R-state alpha subunits and 13-fold for R-state beta subunits.

The beta LeuB10 to Trp mutation resulted in a 75-fold decrease in $K_{O2}$ due to a 5000-fold decrease in $k_{O2}$' and a 60-fold decrease in $k_{O2}$. This mutant also resulted in a 700-fold decrease in $k_{CO}$' and a 65-fold decrease in $k_{CO}$, causing a 40-fold decrease in $K_{CO}$.

TABLE 6

R-State hemoglobin alpha and beta subunit rate and equilibrium constants for oxygen and carbon monoxide binding at 20° C. in 0.1 M bis-tris, 1.0 mM EDTA pH 7.0.

| Hemoglobin | k'$_{O2}$ μM$^{-1}$s$^{-1}$ | | $k_{O2}$ s$^{-1}$ | | $K_{O2}$ μM$^{-1}$ | | k'$_{CO}$ μm$^{-1}$s$^{-1}$ | | $k_{CO}$ s$^{-1}$ | | $K_{CO}$ μM$^{-1}$ | |
| --- | --- | --- | --- | --- | --- | --- | --- | --- | --- | --- | --- | --- |
| | α | β | α | β | α | β | α | β | α | β | α | β |
| $\alpha_{(native)}\beta_{(native)}$ | 29 | 100 | 12 | 22 | 23 | 4.5 | 29 | 7.1 | 0.048 | 0.0072 | 630 | 180 |
| $\alpha_{(wt)}\beta_{(wt)}$ | 16 | 79 | 14 | 33 | 1.1 | 2.4 | 22 | 5.2 | 0.0064 | 0.013 | 410 | 400 |
| $\alpha_{(Val29B10)}\beta_{(wt)}$ | 4.0 | 29 | 5.7 | 20 | 0.8 | 1.4 | 0.24 | 20 | 0.015 | 0.015 | 15 | 130 |
| $\alpha_{(wt)}\beta_{(Bal28B10)}$ | 40 | 101 | 23 | 60 | 1.7 | 1.8 | 1.5 | 47 | 0.012 | 0.014 | 125 | 540 |
| $\alpha_{(Ile29B10)}\beta_{(wt)}$ | 42 | 18 | 55 | 1.3 | 0.76 | 1.4 | 0.29 | 1.5 | 0.017 | 0.018 | 16 | 90 |
| $\alpha_{(wt)}\beta_{(Ile26B10)}$ | 72 | 31 | 15 | 45 | 0.40 | 6.0 | 37 | 0.86 | 0.0076 | 0.018 | 490 | 48 |
| $\alpha_{(Ile29B10)}$ | 60 | | 63 | | 0.96 | | 22 | | 0.0064 | | 230 | |
| $\beta_{(Ile29B10)}$ | | 22 | | 43 | | 48 | | 0.77 | | 0.028 | | 29 |
| $\alpha_{(wt)}\beta_{(Trp26B10)}$ | 18 | 0.018 | 8.6 | 0.5 | 2.1 | .032 | 0.18 | 0.007 | 0.015 | 0.0002 | 18 | 37 |
| $\alpha_{(wt)}\beta_{(wt)}$[a] | 31 | 87 | 242 | 53 | 1.3 | 1.8 | 3.0 | 7.8 | 0.014 | 0.015 | 213 | 500 |
| $\alpha_{(Phe26B10)}$ | 0.88 | | 0.30 | | 29 | | 8.05 | | 0.011 | | 42 | |
| $\beta_{(wt)}$[a] | | 91 | | 52 | | 1.8 | | 5.2 | | 0.014 | | 300 |
| $\alpha_{(wt)}$ | 42 | | 53 | | 0.8 | | 2.9 | | 0.015 | | 19 | |
| $\beta_{(Phe29B10)}$[a] | | 82 | | 12 | | 6.7 | | 0.5 | | 0.03 | | 17 |
| $\alpha_{(Phe28B10)}$ | 0.02 | | 0.29 | | 32 | | 0.05 | | 0.012 | | 42 | |
| $\beta_{(Phe29B10)}$[a] | | 20 | | 12 | | 1.7 | | 1.8 | | 0.025 | | 64 |

[a] These measurements were conducted at pH 7.4 and 25° C.

Data for autooxidation and hemin dissociation from the hemoglobin B10 mutants are presented in Table 7. The Leu29(B10)→Ala, Val, and Ile substitutions increased the rate of hemin dissociation from alpha subunits 2-, 6-, and 4-fold, respectively. In contrast, the Leu28(B10)→Val and Ile substitutions in beta globin decreased $k_{-H}$ 3- to 4-fold. The alpha and beta Val(B10) replacements increased the rate of hemoglobin autooxidation ~2-fold at pH 6. Interestingly, the alpha Ile28(B10) mutant increased $k_{O2}$ 4-fold whereas beta Ile29(B10) had little effect compared to the corresponding wild type subunit.

The Leu(B10)→Ala and Val mutants in alpha and beta subunits caused marked decreases in the protein expression yield as compared to that for wild type hemoglobin. This reduction in stability was greater for the Ala substitutions. Nevertheless, the Ala and Val(B10) substitutions have only small effects on autooxidation and hemin dissociation and the beta Val28(B10) mutant actually increased hemin retention for the beta subunit.

TABLE 7

Rate constants for hemin loss and autooxidation of B10 hemoglobin mutants at 37° C. and 3.0–6.0 μM Heme. Hemin dissociation was measured at pH 7.0 while oxidation was measured at pH 6.0.

| Hemoglobin | α Subunit $k_{-H}$ ($h^{-1}$) | β Subunit $k_{-H}$ ($h^{-1}$) | $k_{OX}$ ($h^{-1}$) |
|---|---|---|---|
| $α_{(wt)}β_{(wt)}$ | 0.42 | 16.0 | 0.087 |
| $α_{(Ala29B10)}β_{(wt)}$ | 1.0 | 11.4 | n.d.[a] |
| $α_{(wt)}β_{(Ala28B10)}$ | n.d. | n.d. | n.d. |
| $α_{(Val29B10)}β_{(wt)}$ | 3.0 | 11.0 | 0.20 |
| $α_{(wt)}β_{(Val28B10)}$ | 0.58 | 4.1 | 0.16 |
| $α_{(Ile29B10)}β_{(wt)}$ | 1.8 | 16.0 | 0.32 |
| $α_{(wt)}β_{(Ile28B10)}$ | 0.6 | 5.0 | 0.11 |
| $α_{(Ile29B10)}β_{(Ile28B10)}$ | 2.3 | 5.0 | n.d. |
| $α_{(wt)}β_{(T/p28B10)}$ | n.d. | n.d. | 0.27 |

[a] n.d. = data collected

Example 8

Hemin dissociation rates for certain mutants are presented below in Table 8. All determinations were made at 5 μM total hemin using 10 μM apomyoglobin. Reactions were carried out in 0.45 M sucrose/0.15 M sodium phosphate, pH 7.0, 37° C., and n=1 unless otherwise noted. Observed rates were estimated by analysis using either an equal amplitude two exponential model, an unconstrained two exponential model, or a single exponential.

In each case the faster rate was assigned to subunits. However, because the observed rates are considerably slower relative to the control molecule, this assignment may be incorrect. Regardless of the exact assignment to specific subunit type, the experimental observation remains: these mutations decrease the observed rate of hemin dissociation from hemoglobin, indicating that they increase the stability of the globin-hemin complex.

TABLE 8

| Hemoglobin | k, $hr^{-1}$ | $k_{d}$, $hr^{-1}$ |
|---|---|---|
| rHb0.1 | 1.3 (0.16) n = 3 | 0.3 (0.02) n = 3 |
| SGE3001 | 0.4 (eqamps) | 0.4 (eqamps) |
| L29F, V67W | 0.3 (1 exp) | 0.3 (1 exp) |
| SGE3002 | 0.4 (eqamps) | 0.2 (eqamps) |
| V62F, V67F, L1061 | 0.3 (n = 2.1 exp) | 0.3 (n = 2, 1 exp) |
| SGE3004 V62L, V67F | 0.7 (n = 2) | 0.12 |

Because the reaction rates for SGE3001 are very slow, only a portion of one half life was collected. Therefore, the rates presented are upper estimates of the true rate. For the current data set, each of the two models used yielded fits of comparable quality and similar rates.

The foregoing description of the invention is exemplary for purposes of illustration and explanation. It will be apparent to those skilled in the art that changes and modifications are possible without departing from the spirit and scope of the invention. It is intended that the following claims be interpreted to embrace all such changes and modifications.

What is claimed is:

1. A method of reducing excess heme in an in vitro system comprising
   a) administering to the system an amount of an apoprotein composition sufficient to reduce the excess heme, the apoprotein composition comprising an alpha or beta globin-like protein comprising at least one mutation consisting of a single amino acid change that stabilizes heme binding.

2. The method of claim 1, wherein the mutation in the globin-like protein is at an amino acid position in either the alpha or beta subunit of hemoglobin selected from the group consisting of B10, CD3, E11, and G8.

3. The method of claim 2, wherein the mutation in the globin-like protein is a mutation in either the alpha or beta subunit of hemoglobin selected from the group consisting of B10→Phe, B10→Val, B10→Ile, CD3→His, E11→Leu, E11→Trp, E11→Phe, and G8→Ile.

4. The method of claim 3, wherein the mutation is selected from the group consisting of:
   (a) Leu28(B10)→Val in beta globin;
   (b) Leu28(B10)→Ile in beta globin;
   (c) Ser44(CD3)→His in beta globin;
   (d) Leu29(B10)→Phe in alpha globin;
   (e) Val67(E11)→Trp in beta globin;
   (f) Val62(E11)→Phe in alpha globin;
   (g) Val67(E11)→Phe in beta globin;
   (h) Leu106(G8)→Ile in beta globin; and
   (i) Val62(E11)→Leu in alpha globin.

5. The method of claim 1, wherein the mutation in the globin-like protein is at an amino acid position in the alpha or beta subunit selected from the group consisting of E7 and B13.

6. The method of claim 5, wherein the mutation in the alpha or beta globin-like protein is selected from the group consisting of E7→Leu, E7→Phe, E7→Met, E7→Trp, B13→Leu, B13→Phe, B13→Met, and B13→Trp.

7. A method of reducing excess heme in a system comprising:
   administering to the system an amount of an apoprotein composition sufficient to reduce the excess heme, the apoprotein composition comprising an alpha or beta globin-like protein comprising at least one mutation consisting of a single amino acid change that stabilizes heme binding.

* * * * *